US008417333B2

(12) United States Patent
Linder et al.

(10) Patent No.: US 8,417,333 B2
(45) Date of Patent: Apr. 9, 2013

(54) PAINLESS NON-STIMULATING LEAD IMPEDANCE MEASUREMENT

(75) Inventors: William J. Linder, Golden Valley, MN (US); Angela M. Muttonen, Forest Lake, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 1034 days.

(21) Appl. No.: 12/333,062

(22) Filed: Dec. 11, 2008

(65) Prior Publication Data

US 2009/0156957 A1 Jun. 18, 2009

Related U.S. Application Data

(60) Provisional application No. 61/007,461, filed on Dec. 12, 2007.

(51) Int. Cl.
  *A61N 1/368* (2006.01)
(52) U.S. Cl.
  USPC .............................................. 607/8; 600/547
(58) Field of Classification Search .................. 600/547; 607/5–8, 28, 63
  See application file for complete search history.

(56) References Cited

U.S. PATENT DOCUMENTS

| 5,755,742 | A | 5/1998 | Schuelke et al. |
| 6,317,628 | B1 * | 11/2001 | Linder et al. ................ 600/547 |
| 6,978,171 | B2 | 12/2005 | Goetz et al. |
| 6,996,436 | B2 | 2/2006 | Allen et al. |
| 7,120,493 | B2 | 10/2006 | Propp et al. |
| 7,970,462 | B2 * | 6/2011 | Lefkov et al. ............... 600/547 |
| 2003/0004552 | A1 | 1/2003 | Plombon et al. |
| 2006/0025828 | A1 | 2/2006 | Armstrong et al. |
| 2009/0024187 | A1 * | 1/2009 | Erickson et al. ............. 607/59 |

FOREIGN PATENT DOCUMENTS

| JP | 2001505093 A | 4/2001 |
| WO | WO-98/19738 A1 | 5/1998 |
| WO | WO-2009075868 A1 | 6/2009 |

OTHER PUBLICATIONS

"International Application Serial No. PCT/US2008/013617, International Search Report mailed Apr. 14, 2009", 3 pgs.
"International Application Serial No. PCT/US2008/013617, Written Opinion mailed Apr. 14, 2009", 7 pgs.
"International Application Serial No. PCT/US2008/013617, International Preliminary Report on Patentability mailed Mar. 22, 2010", 11 pgs.
"Japanese Application Serial No. 2010-537962, Office Action mailed May 29, 2012", (w/ English Translation), 9 pgs.
"European Application Serial No. 08858756.3, Office Action mailed Jul. 20, 2010", 2 pgs.
"European Application Serial No. 08858756.3, Response filed Aug. 12, 2010 to Office Action mailed Jul. 20, 2010", 15 pgs.
"Japanese Application Serial No. 2010-537962, Response filed Sep. 7, 2012 to Office Action mailed May 29, 2012", (w/ English Translation of Amended Claims), 10 pgs.

* cited by examiner

*Primary Examiner* — Christopher D Koharski
*Assistant Examiner* — Frances Oropeza
(74) *Attorney, Agent, or Firm* — Schwegman Lundberg & Woessner, P.A.

(57) ABSTRACT

This document discusses, among other things, an apparatus comprising, a plurality of electrodes configured to deliver defibrillation countershock energy to a subject, an impedance measurement circuit communicatively coupled to the electrodes and configured to measure the impedance between any two of the electrodes using a non-stimulating excitation signal, and a controller communicatively coupled to the impedance measurement circuit and configured to calculate the impedance of a shock vector, wherein the shock vector includes a first electrode and a second electrode electrically connected together, and a third electrode, and wherein the controller calculates the impedance using measured impedances between the three electrodes when none of them are electrically connected.

20 Claims, 3 Drawing Sheets

PAINLESS NON-STIMULATING LEAD IMPEDANCE MEASUREMENT

CLAIM OF PRIORITY

This non-provisional application claims the benefit of priority under 35 U.S.C. §119(e) to U.S. Provisional Patent Application Ser. No. 61/007,461, filed Dec. 12, 2007, the specification of which is herein incorporated by reference in its entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of two or more such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

As these devices continue to increase in complexity, the number of leads and electrodes used by a single device increases. This causes increased complexity in configuring the leads. It is also desirable to determine if a lead develops a poor connection or the lead becomes compromised.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

Figure 1:
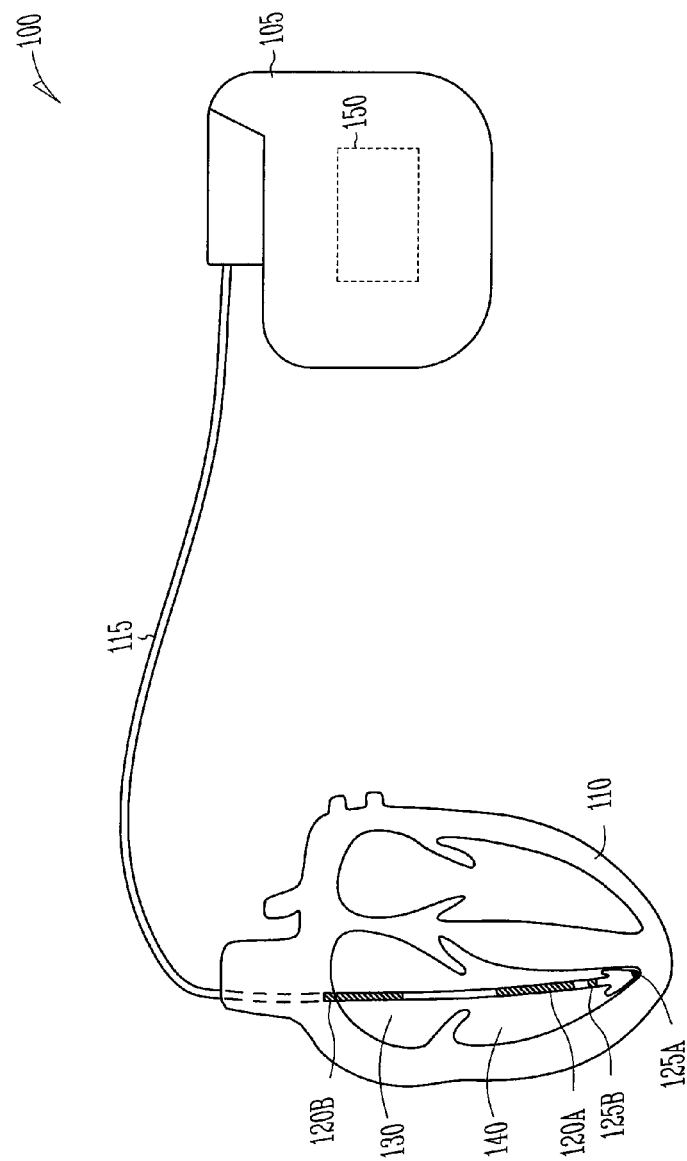
FIG. 1 illustrates an example of portions of a cardiac rhythm management system.

FIG. 1 illustrates an example of portions of a cardiac rhythm management system 100. Various examples of the system 100 include external or implantable pacer/defibrillators, cardioverters, defibrillators, any combination of the foregoing, or any other system using or maintaining cardiac rhythms.

Cardiac rhythm management system 100 can include an implantable cardiac rhythm management device 105 coupled to heart 110 via one or more endocardial or epicardial leadwires, such a pacing leadwire or a defibrillation leadwire 115. Defibrillation leadwire 115 includes one or more defibrillation electrodes, such as for delivering defibrillation countershock ("shock") therapy via first defibrillation electrode 120A or second defibrillation electrode 120B. Defibrillation leadwire 115 can also include additional electrodes, such as for delivering pacing therapy via first pacing electrode 125A (e.g., a "tip" electrode) or second pacing electrode 125B (e.g., a "ring" electrode). Defibrillation electrodes 120A-B and pacing electrodes 125A-B are typically disposed in or near one or more chambers of heart 110. Defibrillation electrode 120A is shown disposed in the right ventricle (RV) 140 and defibrillation electrode 120B is shown disposed in the right atrium (RA) 130.

In the example of FIG. 1, defibrillation leadwire 115 includes multiple conductors that are insulated from each other for providing independent connections between each electrode and cardiac rhythm management device 105. In an example, the defibrillation leadwire is secured to heart 110, such as by a corkscrew, a barb, or similar active or passive fixation mechanism at or near first pacing electrode 125A. In another example, cardiac rhythm management device 105 includes a hermetically sealed housing, a portion of which can provide a conductive can electrode 150 that can operate in conjunction with at least one of the electrodes disposed in heart 110, such as for delivering pacing pulses or defibrillation countershocks or sensing electrical heart activity signals.

In some examples, the electrodes are connectable electrically to form a combined electrode. As an illustrative example, RA electrode 120B and can electrode 150 can be electrically connected. The system 100 provides a defibrillation countershock between RV electrode 120A and the combined electrodes 120B, 150. This is sometimes called a ventricular shock triad vector. Similarly, RV electrode 120A and can electrode 150 can be electrically connected. The system 100 provides a defibrillation countershock between RA electrode 120B and the combined electrodes 120A, 150. This is sometimes called an atrial shock triad vector.

The present system 100 provides, among other things, a cardiac rhythm management system that provides a painless technique of measuring defibrillation lead impedances without delivering a painful high voltage defibrillation countershock. As a result, the defibrillation lead impedance measurement can be performed occasionally, periodically, or even routinely because performing the measurement does not cause discomfort to the patient. In some examples, the system 100 communicates information wirelessly with an external device.

Figure 2:
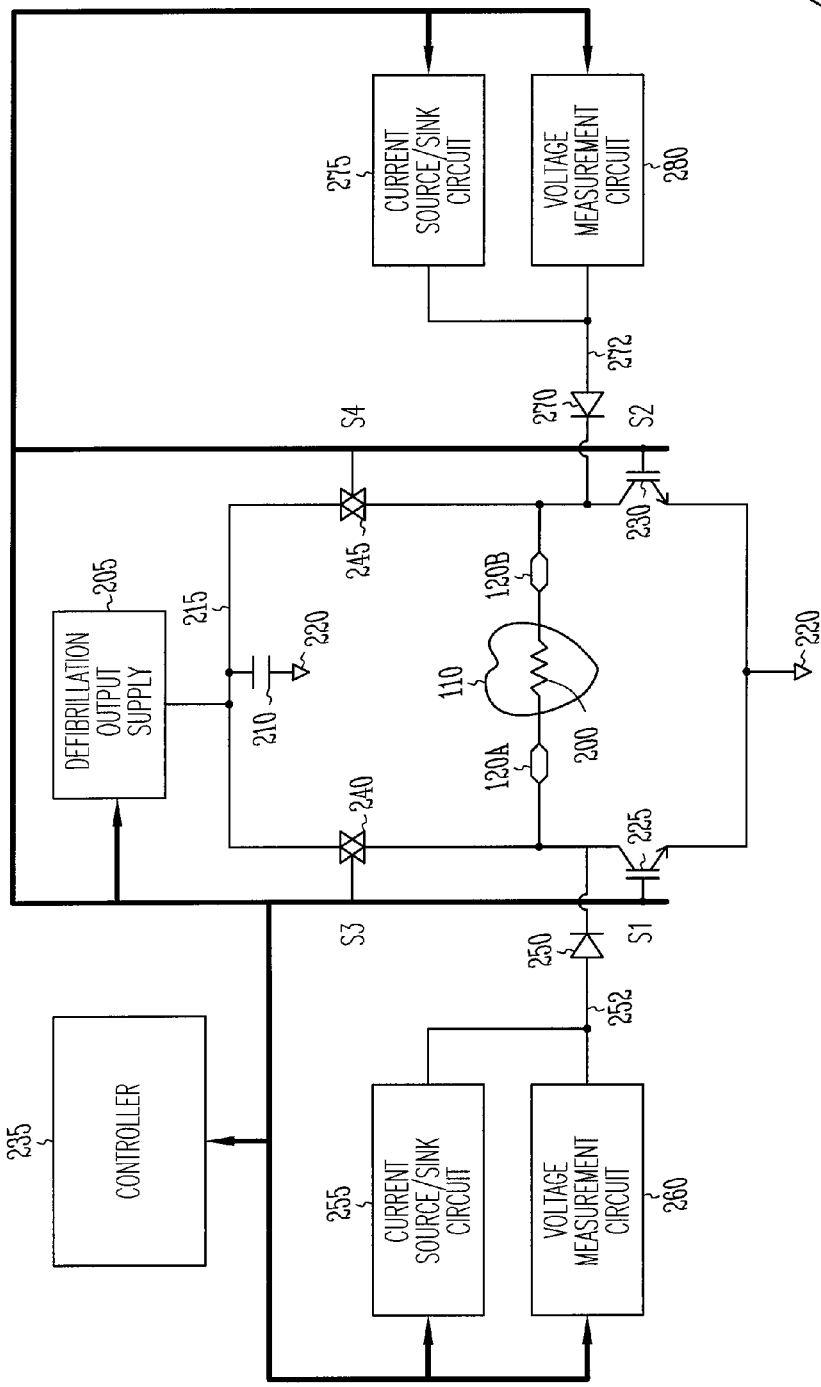
FIG. 2 is an illustration of an example of portions of system to measure lead impedance.

FIG. 2 is an illustration of an example of portions of a system 100 to measure lead impedance. First defibrillation electrode 120A and second defibrillation electrode 120B are illustrated as being coupled to heart 110. Heart resistance 200 is interposed between first and second defibrillation electrodes 120A-B. System 100 includes a defibrillation output supply 205 which generates a defibrillation countershock energy. The defibrillation countershock energy is stored as a high positive voltage (e.g., approximately between 700 Volts and 750 Volts) on a storage capacitor 210 that is coupled between high voltage node 215 and ground node 220.

First switch 225 and second switch 230 are, in an example, insulated gate bipolar transistors (IGBTs) or other switching devices that couple the respective first and second defibrillation electrodes 120A-B to ground node 220. In an example, first switch 225 includes a collector coupled to first defibrillation electrode 120A, a gate coupled to receive a control signal S1, such as from controller 235, and an emitter coupled to ground node 220. Second switch 230 includes a collector coupled to second defibrillation electrode 120B, a gate coupled to receive a control signal S2, such as from controller 235, and an emitter coupled to ground node 220.

Third switch 240 and fourth switch 245 are, in an example, triacs, thyristors, semiconductor-controlled rectifiers (SCRs), four-layer diodes or other switching devices that couple high voltage node 215 to first and second defibrillation electrodes 120A-B, respectively. In an example, control signals S3 and S4 are received from controller 235 to control operation of third switch 240 and fourth switch 245, respectively.

First diode 250 includes a cathode coupled to first defibrillation electrode 120A and an anode coupled at node 252 to lead impedance stimulation and measurement circuits, such as first current source or sink circuit 255 and first voltage measurement circuit 260. Second diode 270 includes a cathode coupled to second defibrillation electrode 120B and an anode coupled at node 272 to lead impedance stimulation and measurement circuits, such as second current source or sink circuit 275 and second voltage measurement circuit 280. In an example, first and second current source/sink circuits 255 and 275, respectively, are combined into a single circuit that is coupled (e.g., multiplexed) to each of the anode of first diode 250, at node 252, and the anode of second diode 270, at node 272. In another example, first and second voltage measurement circuits 260 and 280, respectively, are coupled (e.g., multiplexed) to each of the anode of first diode 250 and the anode of second diode 270. Other examples systems and methods of painless measurement of defibrillation lead impedance are found in Linder et al., U.S. Pat. No. 6,317,628, "Cardiac Rhythm Management System with Painless Defibrillation Lead Impedance Measurement," filed Jan. 25, 1999, which is incorporated herein in its entirety.

To measure impedance of the lead wires that are included in the electrical path that uses electrodes 120A and 120B, the system 100 applies a non-stimulating excitation current between the electrodes and measures the resulting voltage. The excitation current is non-stimulating because it has an amplitude lower than the minimum amplitude for pacing stimulation, i.e., it has a low enough amplitude that it does not trigger a heart depolarization. The measured voltage is divided by the excitation current to obtain the impedance. Because the amplitude has such a low amplitude, the system 200 provides a painless technique of measuring defibrillation lead impedances without delivering a painful high voltage defibrillation countershock.

Figure 3:
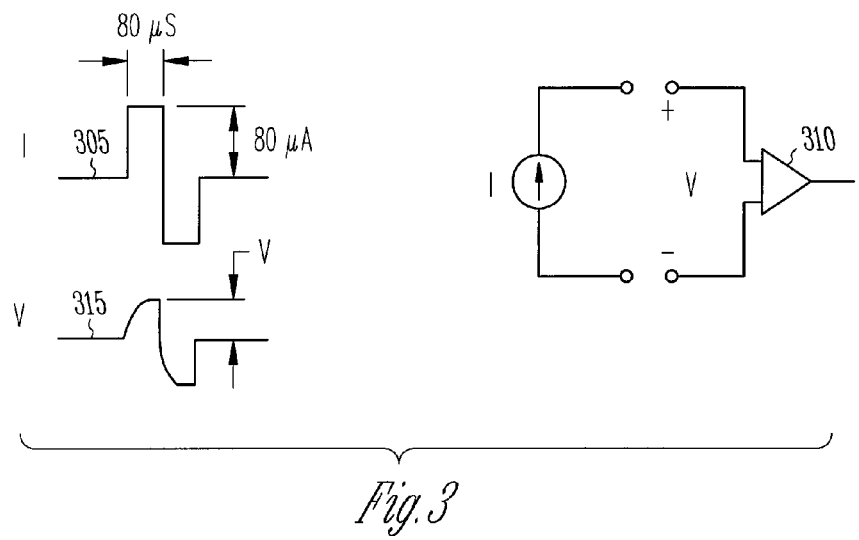
FIG. 3 shows an example of the excitation current I and the resulting voltage V used to measure impedance.

FIG. 3 shows an example of the excitation current I and the resulting voltage V used to measure the impedance. The measurement path can include some capacitance. For this reason, the excitation current I is a biphasic waveform 305 (e.g., a positive phase and a negative phase) to avoid charge buildup at the electrodes 120A, 120B. A voltage measurement circuit 310 measures the resulting voltage V. FIG. 3 also shows a voltage waveform 315 resulting from the excitation current I. A phase pulse of the biphasic waveform 305 should be wide enough to allow time for the charging time constant of the impedance measurement path. In certain examples, a phase pulse is 80 microseconds (μs) wide and has a magnitude of 80 microamps (μA). The measured voltage V is divided by the excitation current I to obtain the impedance.

Returning to FIG. 2, in some examples, the impedance measurement can be a four wire measurement, where the circuit uses two measurement points to provide the non-stimulating excitation current and two measurement points to measure the resulting voltage. In some examples, the impedance measurement can be a two wire measurement, where the circuit uses the same two measurement points to provide the current and to measure the resulting voltage. In some examples, the impedance is measured during a refractory period after a depolarization event, but because the excitation current is non-stimulating, this is not necessary. A refractory period refers to the time interval following a depolarization event when it is difficult or even not possible to induce another depolarization with a stimulus.

The system 100 of FIG. 2 can be generalized to painlessly measure the impedance between any two electrodes in the system. In some examples, system 100 includes a switch matrix which allows any two electrodes (e.g., electrodes 125A, 125B, 120A, 120B, 150 in FIG. 1) to be substituted for electrodes 120A and 120B in the impedance measurement system 200. A physician or other cardiac therapy professional can use the measurement system to measure the impedance for any given defibrillation shock vector. Also, the measurement system can be used to measure the impedance of any pacing vector. For example, the measurement system can measure the impedance between tip electrode 125A and ring electrode 125B. As an another illustrative example, the measurement system can measure the impedance between the tip electrode 125A and the can electrode 150, or the ring electrode 125B and the can electrode 150.

A complication develops when electrodes are electrically connected together. For example, assume the RA electrode 120B and the can electrode 150 are electrically connected and the system 200 is configured to deliver a shock along the vector between the RV electrode 120A and the electrically connected RA-can electrode (e.g., a ventricular shock triad vector). Simply measuring the impedance between the RV electrode 120A and the RA electrode 120B will not provide an accurate measurement of the vector impedance.

Figure 4:
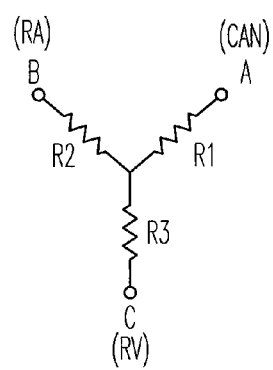
FIG. 4 shows a circuit model of the impedances of the ventricular shock triad vector.

FIG. 4 shows a circuit model of the impedances of the ventricular shock triad vector. Point A is the can electrode 150, Point B is the RA electrode 120B, and Point C is the RV electrode 120A. The impedance seen between the RV electrode 120B and the electrically connected RA-can electrode is the R1 resistance in parallel with the R2 resistance added to the R3 resistance, or (R1∥R2)+R3. Thus, simply measuring the impedance between Point B and Point C would fail to account for the parallel resistance. To determine the impedance, the system measures the impedances between the three points when none of them are electrically connected. The shock triad vector impedance can then be determined using derived equations.

M(AB), M(BC) and M(AC) are the three measurements performed during the shock triad vector measurement, where $$M(AB)=R1+R2,$$

$$M(BC)=R2+R3, \text{ and}$$

$$M(AC)=R1+R3.$$

The three measurements yield three equations with three unknowns that can be written as:

$$R1=\tfrac{1}{2}*(M(AB)-M(BC)+M(AC)),$$

$$R2=\tfrac{1}{2}*(M(BC)-M(AC)+M(AB)), \text{ and}$$

$$R3=\tfrac{1}{2}*(M(AC)-M(AB)+M(BC)).$$

If M1=M(AB), M2=M(BC), M3=M(AC). Then, the shock triad impedance (R1∥R2)+R3 is $$=(((M1*M3)+(M2*M3)+(M2*M1))/2-(M1^2+M2^2+M3^2)/4)/M1.$$

The system performs the three measurements M1, M2, and M3 and the controller 235 is then able to determine the shock triad vector impedance using the derived equations. The atrial triad vector impedance can similarly be determined. The electrodes can then be electrically connected according to the shock triad vector after the three measurements M1, M2, and M3 are completed. The system 200 can communicate the calculated impedance to an external system.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description, with each claim standing on its own as a separate example. The scope of the invention should be determined with reference to the appended claims, along with the full scope of equivalents to which such claims are entitled.

What is claimed is:

1. An apparatus comprising:
a plurality of electrodes configured to deliver defibrillation countershock energy to a subject;
an impedance measurement circuit communicatively coupled to the electrodes and configured to measure the impedance between any two of the electrodes using a non-stimulating excitation signal; and
a controller communicatively coupled to the impedance measurement circuit and configured to calculate the impedance of a shock vector, wherein the shock vector includes a plurality of electrodes electrically connected together to form a combined electrode, and at least one other electrode, and wherein the controller calculates the impedance of the shock vector using impedances measured between pairs of the electrodes when none of them are electrically connected together to form a combined electrode.

2. The apparatus of claim 1, wherein the plurality of electrodes includes a first electrode and a second electrode, wherein the other electrode is a third electrode, and wherein the first, second, and third electrodes form a shock triad vector to deliver the defibrillation countershock energy between the third electrode and the electrically connected first and second electrodes.

3. The apparatus of claim 1, wherein the impedance measurement circuit includes an excitation signal generator configured to provide a non-stimulating biphasic excitation signal.

4. The apparatus of claim 3, wherein the excitation signal generator is configured to provide a biphasic excitation signal having a phase pulse width of less than approximately eighty microseconds (80 μs).

5. The apparatus of claim 3, wherein the excitation signal generator is configured to apply a non-stimulating current having an amplitude of less than approximately eighty microamps (80 μA), and wherein the impedance measuring circuit includes a voltage measurement circuit configured to measure a voltage resulting from the applied current.

6. The apparatus of claim 1, including a controller communicatively coupled to the impedance measuring circuit, wherein the controller is configured to initiate an impedance measurement outside of a refractory period following a depolarizing event.

7. The apparatus of claim 1, wherein the plurality of electrodes electrically connected together includes a can electrode and an electrode disposed in a heart chamber.

8. The apparatus of claim 1, wherein the impedance measurement circuit is included in an implantable cardioverter defibrillator (ICD), and wherein the ICD is configured to communicate the derived impedance to another device.

9. The apparatus of claim 1, wherein the impedance measurement circuit includes a switch matrix circuit to communicatively couple the impedance measurement circuit to electrodes used to deliver electrical pacing therapy.

10. The apparatus of claim 1, wherein the impedance measurement circuit includes a switch matrix circuit and wherein the controller is configured to:
electrically disconnect the plurality of electrodes from each other before initiating an impedance measurement with the non-stimulating excitation signal; and electrically reconnect the plurality of electrodes after the measurement to reform the shock vector.

11. The apparatus of claim 1, wherein the impedance measurement circuit uses two electrodes to apply a non-stimulating excitation current and the same two electrodes to measure the resulting voltage.

12. A method comprising:
forming a shock vector to deliver defibrillation countershock energy to a subject, wherein the shock vector includes a plurality of implantable electrodes electrically connected together to form a combined electrode and at least one other electrode;
measuring impedance between each pair of electrodes in the shock vector using a non-stimulating excitation signal, wherein the impedance is measured while none of the electrodes are electrically connected together to form a combined electrode; and
deriving the impedance of the shock vector using the measured impedances.

13. The method of claim 12, wherein forming a shock vector includes forming a shock triad vector including first and second electrodes electrically connected together and a third electrode, and wherein deriving the impedance includes deriving the impedance between the third electrode and the electrically connected first and second electrode.

14. The method of claim 12, wherein measuring impedance using a non-stimulating excitation signal includes measuring impedance using a biphasic excitation signal.

15. The method of claim 14, wherein measuring impedance using a biphasic excitation signal includes measuring impedance using a biphasic excitation signal having a phase pulse width of less than approximately eighty microseconds (80 μs).

16. The method of claim 14, wherein measuring impedance using a non-stimulating excitation signal includes applying a non-stimulating current having an amplitude of less than approximately eighty microamps (80 μA) and measuring a resulting voltage.

17. The method of claim 12, wherein measuring impedance using a non-stimulating excitation signal includes measuring impedance outside of a refractory period following a depolarizing event.

18. The method of claim 12, wherein forming a shock vector includes forming a shock vector including a can electrode electrically connected to an electrode disposed in a heart chamber.

19. The method of claim 12, including communicating the derived impedance to another device.

20. The method of claim 12, wherein measuring impedance between each pair of electrodes in the shock vector includes:
electrically disconnecting the plurality of electrodes from each other before measuring the impedance with the non-stimulating excitation signal; and
electrically reconnecting the plurality of electrodes to reform the shock vector after the measuring.

* * * * *